United States Patent [19]

Neidleman et al.

[11] Patent Number: 4,859,474

[45] Date of Patent: Aug. 22, 1989

[54] METHOD OF MAKING AN ENZYME SWEETENED CEREAL PRODUCT

[75] Inventors: Saul L. Neidleman, Oakland, Calif.; John A. Maselli, Winston-Salem, N.C.

[73] Assignee: Nabisco/Cetus Food Biotechnology Research Partnership, Emeryville, Calif.

[21] Appl. No.: 101,564

[22] Filed: Sep. 28, 1987

[51] Int. Cl.$^4$ .................................................. A23L 1/10
[52] U.S. Cl. .................................... 426/28; 426/31; 426/44; 426/52; 426/549; 435/94; 435/96; 435/99; 435/945
[58] Field of Search ............... 435/96, 94, 99, 945; 426/28, 31, 549, 52, 44

[56] References Cited

U.S. PATENT DOCUMENTS

| | | | |
|---|---|---|---|
| 897,854 | 9/1908 | Schluter | 426/28 |
| 1,108,555 | 8/1914 | Demeny | 426/28 |
| 1,543,458 | 6/1925 | Takamine, Jr. | 426/28 |
| 2,206,619 | 8/1939 | Schreier | 426/621 |
| 2,555,235 | 5/1951 | Huzenlaub et al. | |
| 3,014,802 | 12/1961 | Hellman et al. | 426/28 |
| 3,262,783 | 7/1966 | Blanchon | 426/28 |
| 3,395,019 | 7/1968 | Kviesitis et al. | |
| 3,880,742 | 4/1975 | James et al. | 426/53 |
| 3,922,201 | 11/1975 | Hebeda et al. | |
| 3,956,506 | 5/1976 | Cloud | 426/28 |
| 3,972,775 | 8/1976 | Wilke et al. | 435/99 |
| 3,998,978 | 12/1976 | Lawrence et al. | 426/285 |
| 4,089,745 | 5/1978 | Antrim et al. | 435/99 |
| 4,247,636 | 1/1981 | Schoenrock et al. | 435/96 |
| 4,286,058 | 8/1981 | Wenger | 435/99 |
| 4,292,331 | 9/1981 | Ostre | |
| 4,299,847 | 11/1981 | Morris | 426/18 |
| 4,371,551 | 2/1983 | Fulger | 426/620 |
| 4,378,432 | 3/1983 | Castelli et al. | |
| 4,379,171 | 4/1983 | Furda | 426/103 |
| 4,431,674 | 2/1984 | Fulger et al. | |
| 4,435,430 | 3/1984 | Fulger et al. | |
| 4,451,567 | 5/1984 | Ishibashi | 435/99 |
| 4,458,017 | 7/1984 | Horwath et al. | 435/96 |
| 4,540,585 | 9/1985 | Priegnitz | |
| 4,596,776 | 6/1986 | Nonaka et al. | 435/96 |
| 4,613,507 | 9/1986 | Fulger | 426/619 |
| 4,663,168 | 5/1987 | Von Fulger | 426/28 |
| 4,710,386 | 12/1987 | Fulger et al. | |

FOREIGN PATENT DOCUMENTS

| | | |
|---|---|---|
| 0231729 | 8/1987 | European Pat. Off. |
| 0124257 | 11/1989 | European Pat. Off. |
| 2215467 | 8/1974 | France |
| 53-062848 | 6/1978 | Japan |
| 57-047465 | 3/1982 | Japan |
| WO86/05953 | 10/1986 | PCT Int'l Appl. |
| 1456262 | 11/1976 | United Kingdom |

OTHER PUBLICATIONS

Hajny and Reese 1969, Cellulases and Their Applications Advances in Chemistry Series 95, ACS, Washington, DC, pp. 16–19.
Bender, 1960, Dictionary of Nutrition and Food Technology, AP New York, pp. 15 and 78.
Bartfay, 1960, Nature 185:924.
Bender, 1960, Dictionary of Nutrition and Food Technology, Academic Press, pp. 8, 53 and 54.
Desrochers, 1981, Applied and Environmental Microbiology 41:222.
Reed, 1966, Enzymes in Food Processing, Academic Press, NY, 88–99 and 269–272.
Bartfay, J., "Glucose-Isomerase in Barley Malt," Nature, vol. 185, No. 4717, pp. 924–925 (Mar. 26, 1960).

*Primary Examiner*—Donald E. Czaja
*Assistant Examiner*—Carolyn Paden
*Attorney, Agent, or Firm*—Elliott L. Fineman; SaraLynn Mandel; Albert P. Halluin

[57] ABSTRACT

A process for producing fructose sweetened cereal products by enzymatically converting a portion of the cellulose fraction in a cereal comprising cereal; fiber to fructose using cellulase and glucose isomerase is claimed. The process may be carried out at moisture contents exceeding 25% (w/w) and moisture contents between about 40% to 80% are preferred.

25 Claims, No Drawings

METHOD OF MAKING AN ENZYME SWEETENED CEREAL PRODUCT

FIELD OF THE INVENTION

The present invention relates to fructose sweetened cereal products and a process for producing such products by enzymatically converting a portion of the cellulose fraction in a cereal flour or meal to fructose using cellulase and glucose isomerase.

BACKGROUND OF THE INVENTION

Cereal grains are a dietary staple in almost every human community and are a source of protein and complex carbohydrates. Cereals contain a high content of starch and cellulosic fiber, and significant amounts of protein.

Throughout their long use as a food staple, cereal grains have been subjected to numerous enzymatic modifications to improve their functionality, primarily by converting starch contained in the cereal product to more easily assimilable or palatable forms. Conversion of fiber in cereals to different forms has received less, but significant, attention in the past because the major portion of fiber can be removed from grains in the grain milling process.

In those processes known in the art in which the cellulose content of the cereal grain is treated, the modifications are primarily directed to improving the accessibility of the starch fraction of the grain for further processing or for recovery of food value from a removed fiber fraction.

In Japanese Publication No. 53-62848, rice is subjected to digestion of cellulose or hemi-cellulose by a solution of enzymes, such as hemi-cellulase, pectinase and cellulase, and solid material is separated from the enzyme solution. The solid material is boiled with water to yield a liquid food.

Japanese Publication No. 57-47363 teaches the production of a cereal tea by treating cereal grains with heat between 100°-200° C. to puff the cereal, followed by treatment with an enzyme such as cellulase. The enzymatically treated cereal is heat dried and than roasted.

U.S. Pat. No. 4,089,745 discloses the treatment of corn hull cellulose with alkali to obtain three fractions and the conversion of the treated cellulose fraction to glucose.

U.S. Pat. No. 4,247,636 discloses treating a mixture of water and flour with $\beta$-glucanase to produce a relatively low viscosity slurry which is treated with amylase, glucoamylase and glucose isomerase to produce a high fructose sweetener.

A process for silage treatment is described in U.S. Pat. No. 4,292,331. Silaged vegetable matter is exposed to enzymes and bacteria or fungi that produce hemi-cellulases, amylase and amyloglucosidase. These enzymes may be suspended on a starch support prior to adding to the vegetable matter. Fermentable sugars are produced which are in turn fermented to lactate by lactobacilli.

In U.S. Pat. No. 4,378,432, vegetable matter is treated with phosphoric acid to hydrolyse cellulose and then enzymes capable of hydrolyzing cellulose and hemi cellulose to produce reducing sugars, whereby a sweetened aqueous solution is obtained.

U.S. Pat. No. 3,395,019 discloses the production of animal feed from oat hulls by treatment of oat hulls, mixed with 50 to 70% water by weight, with alkali, yeast, or enzymes such as catalase, cellulase or amylase. The treatment increases absorbency of the oat hulls for liquid nutrients such as molasses.

U.S. Pat. Nos. 4,431,674 and 4,435,430 disclose enzyme saccharified cereals made from whole grain cereal. In this process, the whole grain is milled and the germ, bran and endosperm fractions are separated. The bran fraction is treated to increase its functionality and endosperm fraction is separately treated enzymatically with $\alpha$-amylase and glucoamylase. The fractions are then recombined. Bran treatment is disclosed as critical to the process, but simultaneously treating all of the cereal fractions enzymatically is taught as decreasing the quality of the dough.

U.S. Pat. No. 2,555,235 teaches the treatment of grain endosperm by steeping vacuum-treated grain in a grain extract at a temperature and pressure to promote enzymatic action. Among the enzymes present in the grains are cellulase and several amylases and glucosidases.

In the present invention, the cellulose component of a flour or meal comprising starch and cellulose fiber, is enzymatically altered to saccaharify the cellulose, and to produce fructose in the treated flour or meal under conditions in which substantially all of the fructose so produced and all, or a substantial portion, of the starch are retained.

BRIEF DESCRIPTION OF THE INVENTION

In one aspect, the invention relates to a process for producing a fructose-sweetened cereal product comprising the steps of:

providing a cereal comprising cereal fiber, moistening the cereal comprising cereal fiber, contacting said moistened cereal comprising cereal fiber with a series of enzymes comprising cellulase and glucose isomerase, incubating said moistened cereal comprising cereal fiber and enzymes for a sufficient period of time to produce fructose and collecting a sweetened cereal product comprising fructose. A cereal flour or meal is preferred as the cereal comprises cereal fiber.

In another aspect of the invention, the process is carried out contacting the moistened cereal flour or meal with cellulase, saccharifying enzymes such as $\alpha$-amylase and amyloglucosidase and glucose isomerase.

In another aspect, the invention relates to a process for producing a sweetened cereal product in which the collected sweetened cereal product is baked.

In yet another aspect, the invention relates to a process for producing a sweetened cereal product in which the cereal flour or meal is moistened with a sucrose solution prior to incubation with the series of enzymes to produce fructose.

In still another aspect, the invention relates to a process for producing a sweetened cereal comprising hydrolysing a portion of or substantially all of the cellulose in said cereal with cellulase and converting the products of said hydrolysis to fructose with glucose isomerase.

In yet another aspect, the invention relates to a sweetened cereal product containing fructose produced by the method of the invention.

DETAILED DESCRIPTION OF THE INVENTION

The present invention concerns a process for making a sweetened cereal product in which a portion of the cellulose fraction, or both the starch and cellulose components of cereal flour or meal are converted into fructose. Prior to milling, cereals have high contents of fiber and starch. Such cereals include a variety of large and small grains including corn, rye, rice, wheat and barley. Other food crops, including soy beans and peanuts, have significant starch and fiber content that may be converted into fructose by the general method according to the invention. Cereals are particularly high in fiber or cellulose as well as containing a significant amount of starch. For example, the pericap, nucellus and tegmen of wheat, all of which together comprise bran, are high in fiber and comprise a significant portion of graham and whole wheat flour. Bran is separated from the endo-sperm of wheat kernels in the milling process to form bread flour and the bran may be collected and separately milled to produce a bran flour. The fiber components of these flours contain significant amounts of cellulose.

In the process according to the invention a moistened milled cereal comprising cereal fiber, preferably a cereal flour or meal comprising cellulose and starch is optionally disrupted and contacted with a series of enzymes which comprises cellulase and glucose isomerase and optionally will further include saccharifying enzymes; the moistened cereal flour or meal with the series of enzymes is incubated for a sufficient period of time to produce fructose, and the cereal product containing fructose is collected. The cellulase enzymes may be cellobiohydralases or endoglucanases, for example.

In the process according to the invention, a substantial portion of the cellulose content of a cereal flour or meal may be enzymatically converted to fructose. The conversion of the cellulose portion of the cereal flour or meal into glucose, and the production of fructose therefrom, leaves intact a significant amount of the starch content of the cereal flour or meal which can be used to maintain texture and formability of the cereal product ultimately produced from the treated flour or meal. Alternatively, a portion of the starch may also be saccharified, in addition to producing glucose or other sugars or with the enzymatic action of glucose isomerase, additional fructose, while still maintaining a significant amount of starch which may be desirable for texturing and forming operations of the treated cereal.

Fructose is known to have a higher degree of sweetness than glucose or sucrose. Thus, high fiber cereals may be produced having a desired degree of sweetness while retaining a relatively low digestable calorie content since it is not necessary to saccharify starch in the process according to the invention. Accordingly, one product of the process of the invention is an enzymatically sweetened-low-calorie-high fiber cereal product.

In greater detail, the process according to the invention entails the production in a moistened cereal of fructose by enzymatic treatment. The cereal will generally be milled or subjected to some process whereby the cereal grain is fractured, crushed, or disrupted into small pieces. Such milled cereal grain is preferably in the form of a coarse or fine flour or meal produced from a starch and cellulose containing cereal grain. Such 9rains include large and small grains including corn, rice, wheat, oats, barley and rye. The various flours and meals that may be produced from these grains are the material used for the process according to the invention. Flours and meals produced from these grains and which are appropriate for the production of breakfast cereals are generally known. With respect to flours, those produced from wheat are preferred, and in particular, bran flours, graham flour and whole wheat flour are appropriate. Bran flour is especially preferred.

In general, the flour will be supplied in dry form having a water or moisture content of 20% or less, in general about 10%. Prior to or concurrent with enzymatic treatment according to the invention, the moisture content of the flour is increased. In general, the moisture content is increased sufficiently to permit the activity of the series of enzymes mentioned above, all of which in general function in an aqueous or hydrated environment. Moisture content is determined as the weight percent $H_2O$ of the total mixture. The moisture content will range from about 25% and up. A moisture content of between about 40% and about 80% is preferred for sustaining the activity of series of enzymes mentioned above. The moisture content may be varied depending upon the type of flour used, the texture of the final cereal product desired, and the speed of the saccharification and fructose formation reactions desired, but in general, the moisture content will not exceed the amount of water that the flour or meal can absorb. At moisture content between about 55 and 60% using a bran flour, a friable sweetened cereal product is obtained. The moisture content of the flour or meal is adjusted by the addition or removal of water to the flour. If the flour or meal is presoaked in an aqueous solution or in water prior to the addition of the enzyme series, it may be desirable to remove water by conventional means such as decanting, blotting, pressing, straining, and heating or a combination of these conventional means. If a dry flour or meal is used, moisture content may be adjusted by the addition of solutions containing water. Such a solution may include aqueous enzymes, including the cellulases and glucose isomerase mentioned above, or optionally, in addition, the amylases and amyloglucosidases. Alternatively, or in addition, the flour may be moistened by aqueous flavoring syrup. Such flavoring syrups may contain sucrose, fruit extracts, and the like. The addition of such aqueous sucrose solutions, however, is not required in the process according to the invention, as substantial amounts of glucose and fructose are developed from the flour by enzymatic action.

It is preferred in the process according to the invention to conduct the enzymatic treatment of the cereal flour or meal with moisture content sufficient to sustain the activity of the series of enzymes, but in general, it is not desirable to add so much water to the cereal grain or flour that excess water may be recovered from the moistened grain or flour by draining after the enzymatic treatment. Moisture contents so great as to permit drainage of excess water will generally lead to a loss of soluble sugars produced as a result of the enzymatic treatment. Therefore, it is desirable to moisten the cereal grain or flour with no more solution of water than the cereal grain or flour can completely absorb.

In preparing flour or meal for further processing, the flour or meal is disrupted to partially alter the starch and cellulose contained in the flour or meal. In general, the disruption process involves the application of heat, and preferably moist heat. Thus, disruption may be carried out by steaming, steam injection, pressure cooking in a closed vessel or, less preferably, by the application of dry heat. Chemical disruption process such as treating with mild alkali are also known.

The addition of the enzyme series to the cereal meal or flour can occur at various points in the process for producing the sweetened cereal product according to the invention. In general, the enzyme may be added before, after, or during disruption of the flour or meal. It is generally preferred to contact the flour or meal with the series of enzymes after disruption. Without being bound by this theory, the disruption of the flour or meal is believed to increase the microaccessability of enzyme to substrate in the disrupted flour and thus maximizes both the fructose yield and the availability of sugars and smaller saccharides for browning reactions if the sweetened cereal product is eventually cooked.

The series of enzymes may alternately be added prior to disruption. If the series of enzymes is added at this point in the process, the subsequent disruption step can be adjusted to maintain enzyme activity for a portion of the disruption cycle by adjusting the rate at which the temperature of the enzyme-cereal flour or meal mixture is raised. Of course, the disruption step may be used to eventually substantially or completely inactivate the series of enzymes added to the flour or meal if the series of enzymes is added prior to the disruption step.

The series of enzymes may alternately be added during the disruption step. If the series of enzymes is added during the heat disruption step, the amount of each enzyme added and the rate of heating may be adjusted to obtain the desired level of fructose formation in the final product. In each case, when the series of enzymes is added before or during the heat disruption step, and the heat of the disruption step is used to increase the activity of the series of enzymes, it may be desirable to use thermostable enzymes. Such thermostable enzymes are generally known and may be obtained from microorganisms that are found in high thermal environments. A thermostable glucose isomerase and glucoamylase has been described, for example, in U.S. Pat. Nos. 4,532,208 and 4,536,477, respectively. Furthermore, the use of thermo-stable enzymes permits the process of the invention to be carried at temperatures generally higher than 75° C. and thus may be useful in shortening the time necessary for producing fructose in the sweetened cereal product.

The order in which the members of the series of enzymes is added to the moistened cereal flour or meal is also significant in the process according to the invention. In general, the enzymes may be added to the disrupted or non-disrupted flour or meal all at one time or in an order wherein the glucose isomerase enzyme is added last. It is desirable to achieve a steady state of glucose isomerase activity. similar to that achieved by a slow feed of glucose for conversion into fructose. The concentration of fructose produced under these conditions is not so great as to inhibit the formation of fructose from glucose. In general, when the flour substrate is in a moisture condition of 75% water or less, it is desirable to add all the enzyme at once. Under these conditions, glucose produced by cellulase or by the combination of cellulase and saccharifying enzymes such as α-amylase and amyloglucosidase is converted to fructose by glucose 5 isomerase at a rate essentially equivalent to the rate at which glucose is produced. In general, it is desirable to add an excess of glucose isom-erase. Incubation of the enzymes with the moistened cereal may be carried out at a temperature between 250° C. and 80° C.

The fructose sweetened cereal product produced by the process of the invention is collected and may be dried, for example, by baking at a temperature about 250° C. and 450° F.

The invention will be better understood in connection with the following examples, which are intended by the inventor to be merely exemplary and non-limiting.

EXAMPLE 1

White wheat bran was soaked in distilled deionized water for approximately 60 hours at 5° C., was squeeze dried through cheese cloth, and ground to a fine mush. 0.25 grams of the wetted bran was placed in a 50 ml closed vial and enzyme was added as shown below. Total volume was 10 ml and the final pH was 5 or 6 adjusted with 1 NHCl. The reaction was run in duplicate at 40° C. with shaking for 3.0 hours. At the end of the reaction, the sample was analyzed for carbohydrate content using a Boehringer-Mannheim food analysis kit (catalogue No. 139106). The enzyme preparations were as follows:

A cellulase enzyme preparation (referred to as CEL in some of the following tables) from *Trichoderma reeseii* in 50 mM sodium acetate, 3 mM sodium azide buffer at pH 5.5 with a total specific activity of approximately 104 units/ml was used. The cellulase enzyme had the following activity distribution (U/mg enzyme): Avicel (crystallized cellulose) 0.3; phosphoric acid swollen cellulose (PSC) 3.6 carboxymethyl cellulose 3.6; cellobiose 0.3; paranitrophenyl-Dglucoside (PNPG) 0.3; Xylan 1.2 Mannan 0.3.

Glucose isomerase (Spezyme) preparation in 50 mM sodium phosphate, 10 mM magnesium sulfate, 1 mM $COCl_2$, pH 6.0 having a specific activity of 110 units/ml was used. Results are shown in Table I.

TABLE I

| Reaction | Bran (g) | CEL | GI | Buffer | Avg. Yield (gm/L) D-Glucose | D-Fructose | % Dry Weight Fructose |
|---|---|---|---|---|---|---|---|
| 1 | 0.25 | — | — | 10 ml | 0 | 0 | |
| 2 | 0.25 | 5 ml | — | 5 ml | .534 | 0 | |
| 3 | 0.25 | 5 ml | 5 ml | — | .50 | 0.052 | ~9% |

An additional 5 ml aliquot of glucose isomerase was added to Reaction vessel 3. Reaction vessels 2 and 3 were incubated at 05° C. overnight without shaking. In addition, a duplicate set of flasks identical to Reaction 3 was run overnight at 05° C. without shaking. Yield were as follows:

| Reaction | D-Fructose | D-Glucose | % Dry Weight Fructose |
|---|---|---|---|
| 2 | 0 | .534 | 0 |
| 3 (+GI) | .12 | .47 | ~20% |
| 3 (duplicate) | 0.05 | .71 | ~6.6% |

EXAMPLE 2

The following reactions were run using the same enzyme preparation as in Example 1 at 45° C. without shaking overnight one flask per preparation. Both white and red wheat bran flour, prepared as in Example 1, were used.

1. White bran flour

| Re-action | Bran Flour | Cel | GI | Buf-fer | Glu-cose | Fruc-tose | % Dry Weight Fructose |
|---|---|---|---|---|---|---|---|
| 1 | 0.25 gm | — | — | 10 ml | 0 | 0 | |
| 2 | — | 5 ml | 5 ml | — | 0 | 0 | |
| 3 | 0.25 gm | 5 ml | — | 5 ml | .86 | 0 | |
| 4 | 0.25 gm | 5 ml | 5 ml | — | .86 | 0.09 | ~9.3% |

2. Red Bran Flour

| Re-action | Bran Flour | Cel | GI | Buf-fer | Glu-cose | Fruc-tose | % Dry Weight Fructose |
|---|---|---|---|---|---|---|---|
| 1 | 0.25 | — | — | 10 | 0 | 0 | |
| 2 | — | 5 ml | — | 5 | 0 | 0 | |
| 3 | 0.25 | 5 ml | — | 5 | .66 | 0 | |
| 4 | 0.25 | 5 ml | 5 | — | .62 | .08 | ~11.4% |

In both experiments the reaction products containing glucose or glucose/fructose were darker than the reaction products without glucose or fructose.

EXAMPLE 3

In both experiments the reaction products were indicated in Example 1. Reactions were run at a total volume of 20 ml in a 250 ml Erlenmeyer flask. The bran flour was not prewashed. Temperature was 45° C. for 20 hours then 60° C. for four hours; no shaking for 20 hours, the 75 rpm for four hours.

| Re-action | Bran (g) | ML Cellulase | GI | Buffer | Yield g(L) 24 hr. Glucose | Fructose |
|---|---|---|---|---|---|---|
| 1 | 5 | 5.5 | 1.1 | 13.4 | 11.0 | 10.8 |
| 2 | 5 | — | — | 15 | 0 | 0 |
| 3 | — | 5.5 | 1.1 | 13.4 | 0 | 0· |

Time course of yield for Reaction (g/l)

| | Hours | | | | | | |
|---|---|---|---|---|---|---|---|
| | 0 | 1 | 2 | 3 | 20 | 22 | 24 |
| D-glucose | 0.9 | 4.0 | 5.1 | 4.6 | 9.9 | 10.3 | 11.0 |
| D-fructose | 0.06 | 2.2 | 3.5 | 4.3 | 9.4 | 10.1 | 10.8 |

Assuming an approximate cellulose content of 11.3% the percent conversion of cellulose to glucose and fructose is 77%.

EXAMPLE 4

Enzymes, buffers and bran flour were the same as in Example 2. In addition, the following enzymes were used: α-amylase (1,4-α-D-glucanglucanohydrolase E.C. 3.2.1.1) from B. licheniformis (Sigma) (referred herein as αA), amyloglucosidase, exo 1,4 α-glucosidase 1,4 α-D-glucan glucohydrolase E.C. 3.2.1.3 for *Aspergillus oryzae* (Sigma) referred to as GA). α-Amylase concentration was 11040 U/ml, GA was 1400 U/ml, GI was 2250 U/ml, and cellulase was 18.9–227 U/ml. Buffer was the same as that used for glucose isomerase: 50 mM NaPO$_4$, pH 6.0, 10 mM MgSO$_4$, 1 mM CoCl$_2$. A flavoring syrup having the following composition was used in parts per hundred (ppC): liquid sucrose (67 brix) 34 ppC; NaCl 2.0; fig and prune concentrate 2 ppC; vitamin solution including niacinamide, B1, B6, B2, and C .8 ppC; balance water.

The following protocol was used: Into a 1 liter breaker bran (102.5 gm) and flavor syrups (46.6 gm (41 ml) were measured. The material was thoroughly mixed and loosely covered with aluminum foil. The mixture was autoclaved at 121° C., 15 psi for 25 minutes and then cooled to room temperature. The mixture was distributed in 39 gm aliquots into 1 liter beakers. The aliquots were treated as follows:

| A | |
|---|---|
| Cellulases | 2500 U (7 ml) |
| Glucose isomerase | 2500 U (1.6 ml) |
| Buffer, pH 5.5 | 11.4 ml |

Incubated at 45° C., no shaking, moisture saturated atmosphere, tightly covered with foil.

| B | |
|---|---|
| α-amylase | 2500 U (0.23 ml) |
| Amyloglucosidase | 2500 U (1.8 ml) |
| Glucose isomerase | 2500 U (1.6 ml) |
| Cellulases | 2500 U (7 ml) |
| Buffer, pH 5.5 | 9.37 ml |

| C | |
|---|---|
| Buffer, pH 6.0 | 20 ml |

Incubated at 60° C. in a water bath, no shaking, tightly covered with foil.

Samples were taken periodically and frozen. Assay for D-glucose and D-fructose were carried out on 0.2 gm of each samples as described above. Dry weights of various samples were determined by heating to 150° C. for two hours in aluminum pans using a drying oven.

D-glucose/D-fructose analyses: These were done as described in the previous examples. The bran used for the study had a moisture content ~50–60%. Therefore, each reaction beaker contained 23.1 gm dry bran; and each sample analyzed was 0.1084 gm, the bulk of which was dry bran.

Results: Production of D-glucose/D-fructose:

| | gm/L | | | | |
|---|---|---|---|---|---|
| | 1 hr. | 2 hr. | 5 hr. | 22 hr. | 24 hr. |
| 1. Reaction A (cellulases/glucose isomerase) | | | | | |
| D-glucose | 12.4 | 12.0 | 8.3 | 12.2 | 15.0 |
| D-fructose | 1.2 | 1.6 | 2.2 | 4.2 | 5.1 |
| % conversion of cellulose | ~72 | ~72 | ~53 | ~86 | ~106 |
| 0.0 84 gm aliquot | | | | | |
| 2. Reaction B (amylases/cellulases/glucose isomerase) | | | | | |
| D-glucose | 19.4 | 19.9 | 13.3 | 18.8 | 21.6 |
| D-fructose | 2.4 | 4.1 | 4.5 | 4.9 | 9.6 |
| % conversion of starch + cellulose in 0.084 gm aliquot | ~34 | ~37 | ~28 | ~43 | ~48 |
| 3. Reaction C (control) No D-glucose or D-fructose. | | | | | |

The mixtures in the enzyme-treated instances were darker and stickier than the control, due to the high-monosaccharide content and browning reactions. They had a pleasant aroma.

Samples of beakers of Reactions B and C contents were baked for 20 minutes at 150° C. The resultant products were very different in obvious properties. The aroma of the enzyme-treated sample was much more intense and pleasant that of the control and the enzyme-treated samples was darker and particles adhered to each other, whereas the control was lighter and particles were discrete.

What is claimed is:

1. A process for producing a sweetened cereal product comprising:
   (a) moistening a cereal grain by adding an aqueous solution to a cereal grain containing cellulose and starch in an amount sufficient to support conversion by enzymes of the cellulose and starch to fructose;
   (b) disrupting the moistened cereal produced in step (a) to an extent effective to promote the enzymatic conversion of the cellulose and starch to fructose;
   (c) adding to the disrupted, moistened cereal produced in step (b) enzymes effective to convert cellulose and starch to glucose and the glucose to fructose to produce a moistened cereal and enzyme mixture;
   (d) incubating said moistened cereal and enzyme mixture for a sufficient period of time and at a sufficient temperature to convert the cellulose and starch in said cereal to fructose while retaining a sufficient amount of starch for texture and formability in the resulting cereal product enriched in fructose; and
   (e) collecting said cereal product enriched in fructose.

2. The process of claim 1 wherein said enzymes include cellulases, glucose isomerases, alph-amylases and amylo-glucosidases.

3. The process of claim 1 wherein said step of disrupting comprises heating under pressure.

4. The process of claim 3 wherein said heating is carried out prior to addition of the enzymes.

5. The process of claim 3 wherein said heating is carried out concurrently with said step of incubating.

6. The process of claim 3 wherein said heating is carried out after said step of incubating.

7. The process of claim 1 further including a drying step after said step of collecting.

8. The process of claim wherein said drying step includes baking.

9. The process of claim 8 wherein said baking step is carried out at a temperature in the range of between about 250° and 450° F.

10. The process of claim 8 wherein said baking step is carried out at a temperature of about 300° F.

11. The process of claim 1 wherein said step of disrupting comprises treatment with alkali.

12. The process of claim 3 wherein said enzymes comprise cellulase and glucose isomerase and said cellulase enzyme is added to the disrupted, moistened cereal before the glucose isomerase.

13. The process of claim 1 wherein said enzymes are cellulase, alpha-amylase and amylo-glucosidase and said cellulase enzyme and alpha-amylase and amylo-glucosidase enzymes are added to the disrupted, moistened cereal before glucose isomerase.

14. The process of claim 2 wherein said step of incubating is carried out at a temperature of between about 25° and 80° C.

15. The process of claim 2 wherein said step of incubating is carried out at a temperature of between about 45° and 60° C.

16. The process of claim 2 wherein said cellulases are selected from the group consisting of cellobiohydrolases and endogulcanases.

17. The process of claim 1 wherein said cereal grain is in the form of cereal flour or meal.

18. The process of claim 17 wherein said cereal is selected from the group consisting of bran flour, bran meal, graham flour, graham meal, whole wheat flour and whole wheat meal.

19. The process of claim 1 wherein said step of moistening and said step of adding the enzymes are carried out concurrently.

20. The process of claim 1 wherein the amount of aqueous solution added is such that substantially all of the solution is absorbed by said cereal.

21. The process of claim 20 wherein said moistened cereal has a moisture content of about 40% to 75% weight/volume.

22. The process of claim 20 wherein said moistened cereal has a moisture content of about 60% weight/volume.

23. The process of claim 1 wherein said enzymes to convert cellulose to glucose are cellulases.

24. The process of claim 11 wherein said enzymes effective to convert starch to glucose are selected from the group consisting of alpha-amylases and amyloglucosidases.

25. The process of claim 1 wherein said enzyme effective to convert glucose to fructose is glucose isomerase.

* * * * *